(12) United States Patent
Mo et al.

(10) Patent No.: US 6,841,574 B2
(45) Date of Patent: Jan. 11, 2005

(54) TOPICAL STABILIZED PROSTAGLANDIN E COMPOUND DOSAGE FORMS

(75) Inventors: Y. Joseph Mo, Princeton, NJ (US); Daniel W. Frank, Broomall, PA (US)

(73) Assignee: NexMed Holdings, Inc., Robbinsville, NJ (US)

( * ) Notice: Subject to any disclaimer, the term of this patent is extended or adjusted under 35 U.S.C. 154(b) by 0 days.

(21) Appl. No.: 10/336,481

(22) Filed: Jan. 3, 2003

(65) Prior Publication Data

US 2004/0131664 A1 Jul. 8, 2004

(51) Int. Cl.[7] .................. A61K 31/19; A61K 31/557; A61K 9/00; A61F 13/00; A61L 15/16
(52) U.S. Cl. .................. 514/573; 424/400; 424/401; 424/433; 424/444; 424/484; 424/486; 424/488; 514/947; 514/953
(58) Field of Search .................. 424/400, 401, 424/433, 434, 444, 443, 449, 484, 486, 488; 514/573, 947, 953

(56) References Cited

U.S. PATENT DOCUMENTS

| | | | | |
|---|---|---|---|---|
| 3,826,823 A | * | 7/1974 | O'Rourke et al. | 514/559 |
| 3,875,300 A | * | 4/1975 | Homm et al. | 424/433 |
| 3,883,576 A | * | 5/1975 | Axen | 560/121 |
| 4,136,162 A | * | 1/1979 | Fuchs et al. | 424/443 |
| 4,483,846 A | * | 11/1984 | Koide et al. | 424/433 |
| 4,552,751 A | * | 11/1985 | Inaba et al. | 424/449 |
| 4,767,787 A | * | 8/1988 | Kawata et al. | 514/573 |
| 4,777,046 A | * | 10/1988 | Iwakura et al. | 424/435 |
| 5,017,382 A | * | 5/1991 | Embrey et al. | 424/486 |
| 5,380,760 A | * | 1/1995 | Wendel et al. | 514/573 |
| 5,973,002 A | * | 10/1999 | Frolich et al. | 514/530 |
| 6,046,244 A | * | 4/2000 | Buyuktimkin et al. | 514/785 |
| 6,323,241 B1 | * | 11/2001 | Yeager et al. | 514/573 |
| 6,593,369 B2 | * | 7/2003 | Neal | 514/573 |

FOREIGN PATENT DOCUMENTS

WO  WO 96/34633 A1 * 11/1996

* cited by examiner

Primary Examiner—Michael G. Hartley
Assistant Examiner—Marina Lamm
(74) Attorney, Agent, or Firm—Olson & Hierl, Ltd.

(57) ABSTRACT

Compounds of prostaglandin E group (PGE compounds) are stabilized as non-aqueous compositions that include the compound together with a bulking agent that can be a non-aqueous liquid or a solid in a sheet, film or powder form. The composition can optionally include a skin penetration enhancer. A non-aqueous, solid dosage form comprises a PGE compound substantially uniformly distributed in a carrier sheet or film.

2 Claims, No Drawings

TOPICAL STABILIZED PROSTAGLANDIN E COMPOUND DOSAGE FORMS

TECHNICAL FIELD

This application relates to room temperature stable, non-aqueous prostaglandin E compound dosage forms suitable for the treatment of sexual dysfunction in male as well as female patients.

BACKGROUND OF THE INVENTION

Prostaglandins may exhibit vasodilation or vasoconstriction, smooth muscle stimulation or depression. Prostaglandins of the E group, such as Prostaglandin $E_1$ ($PGE_1$) has been reported as having utility for the treatment of sexual erectile dysfunction when injected intracavernously as an aqueous solution in physiological saline, Mahmond et al., J. Urology 147:623–626 (1992), or applied topically. However, the prostaglandins, such as $PGE_1$, are relatively insoluble in water, and are also relatively unstable. As a result, prostaglandin solutions for injection are prepared shortly prior to use, a relatively inconvenient expedient.

Attempts to stabilize $PGE_1$ in aqueous systems by the use of α-cyclodextrin or β-cyclodextrin complexes have been reported. Wiese et al., J. Pharm. Sciences 80:153–156 (1991); Szejtli, J., "Industrial Applications of Cyclodextrins," Inclusion Compounds III, Academic Press, London, England (1984), pp. 355–368. However, even the aqueous $PGE_1$ preparations so-stabilized have a relatively short shelf life that limits their practical utilization.

It has now been found that the stability of prostaglandins of the E group can be substantially enhanced without sacrificing bioavailability by the use of specific non-aqueous pharmacologically acceptable compositions that can be stored in a separate compartment from a topical delivery vehicle and combined with the delivery vehicle just prior to use.

SUMMARY OF THE INVENTION

Compounds of prostaglandin E group are stabilized as non-aqueous compositions that include the compound together with a bulking agent that can be a non-aqueous liquid, or a solid in sheet, film, or powder form. Optionally, a skin penetration enhancer can be present.

A preferred non-aqueous, solid dosage form comprises a compound of prostaglandin E group substantially uniformly distributed in a carrier sheet or film. A predetermined size portion of this sheet or film can be introduced directly into a moist body cavity to release the prostaglandin compound. Alternatively a predetermined size portion of the sheet or film which includes a prostaglandin compound can be dissolved in an aqueous or non-aqueous solvent that serves as a physiologically compatible delivery vehicle for the prostaglandin compound. For topical applications, the topical delivery vehicle is viscous and substantially non-flowing, such as a cream, gel, or ointment.

In an alternative preferred embodiment a packaged, paired compartment dosage form comprises a sealed actives compartment and a sealed inerts compartment. Compound of prostaglandin E group is contained within the actives compartment together with a bulking agent, and optionally a skin penetration enhancer. A physiologically compatible viscous topical delivery vehicle is contained within the inerts compartment and is combined with the contents of the actives compartment prior to use, preferably just prior to use. A skin penetration enhancer can be included in the inerts compartment in addition to, or in lieu of, a skin penetration enhancer in the actives compartment.

The present, dosage forms containing stabilized compound of the prostaglandin E group are useful for amelioration of sexual dysfunction in human patients, e.g., male impotence, premature ejaculation, female sexual arousal disorder, and the like.

DESCRIPTION OF THE PREFERRED EMBODIMENT

Prostaglandin E is a known compound that can be represented by the formula

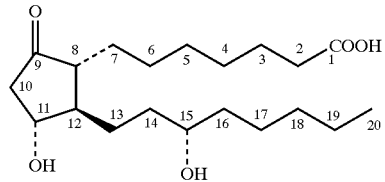

Compounds derived from the foregoing structure and having the 9-oxo, 11α-hydroxy substituents as well as unsaturation in the side chains are known as compounds of the prostaglandin E group, hereinafter collectively referred to as PGE compounds. The compounds of this group include prostaglandin $E_1$ ($PGE_1$) represented by the formula

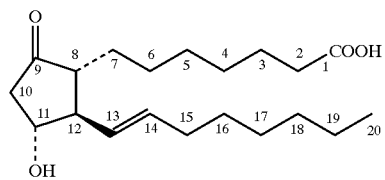

prostaglandin $E_2$ (or $PGE_2$) represented by the formula

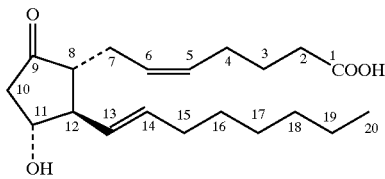

prostaglandin $E_3$ (or $PGE_3$) represented by the formula

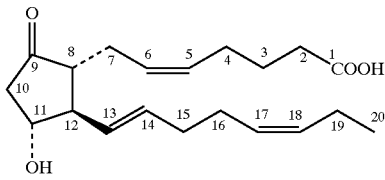

as well as the pharmaceutically acceptable salts thereof.

PGE compounds have useful therapeutic activity as vasodilators and have been utilized to treat male and female sexual disorders, to control lipid metabolism, to treat ulcers, to treat inflammatory skin lesions, and the like therapeutic applications.

PGE compounds are relatively unstable, however, and tend to decompose, especially in aqueous solutions or in an aqueous environment. It has now been found however, that these compounds can be effectively stabilized while providing sheet-form compositions that can be readily handled and metered to provide convenient dosage forms for topical administration either directly or combined with a viscous topical delivery vehicle such as a cream, gel, ointment, and the like.

PGE compounds can be incorporated as substantially uniformly distributed solids in a sheet-form material, i.e., sheet or film, of a physiologically compatible polymeric material, e.g., a cellulosic ether such as hydroxypropyl cellulose, hydroxypropyl methyl cellulose, and the like, a polysaccharide such as starch, polyvinylpyrrolidone, and the like. Sheet-form materials having a thickness of no more than about 10 mils are commonly referred to as films, and those having a thickness of more than about 10 mils are commonly referred to as sheets. The term "sheet-form" as used herein and in the appended claims refers to sheets as well as films. The sheet-form material can be a solid or a porous material, e.g., a sponge or the like. The sheet-form material containing a PGE compound dispersed therein can be converted into discs, tablets, pellets, and the like, if desired.

These sheet-form articles of manufacture can be water soluble for direct introduction into moist body cavities or soluble in a non-aqueous physiologically compatible solvent for the preparation of a cream or ointment suitable for topical application. The water soluble moiety of the prostaglandin-bearing sheet-form material can also be utilized, of course, for the preparation of aqueous gels based on a polycarbophil, a polyoxyethylene-polyoxypropylene block copolymer, e.g., the so-called poloxamers, and on mixtures thereof, as well as non-aqueous gels based on the polysorbates, liquid block copolymers of propylene oxide and ethylene oxide, and the like.

If desired, the PGE compound-bearing sheet form materials of the present invention can also include physiologically compatible plasticizers, solubility enhancers (e.g., hydroxypropyl-beta-cyclodextrin), and the like.

These PGE-bearing sheet-form materials can be prepared by first forming a solution of the desired PGE compound in a non-aqueous solvent such as a $C_2$ to $C_4$ aliphatic alcohol, e.g., methanol, ethanol, propanol, isopropanol, n-butanol and the like, together with the polymeric material, with or without a skin penetration enhancer, then casting the solution continuously on a roll or batchwise in a shallow dish or pan, and thereafter evaporating the solvent therefrom. The resulting sheet or film has the PGE compound substantially uniformly distributed throughout in an non-aqueous medium that can be readily subdivided and apportioned into desired unit doses each having a predetermined PGE content. The cast sheet or film can also be retained on a solid surface for storage and dissolved immediately prior to use.

The foregoing unit doses can be utilized to provide packaged, paired compartment dosage forms in which an actives compartment contains the PGE compound unit dose and an inerts compartment contains the delivery vehicle for a topical application. In the packaged, paired-compartment dosage forms embodying the present invention, the actives compartment can also contain the PGE compound together with a bulking agent in a non-aqueous liquid, particulate or granular form. Suitable liquid bulking agents are silicone oils such as the polydimethylsiloxanes, e.g., cyclomethicone USP, dimethicone USP, and the like. Suitable solid bulking agents for this particular purpose are the cyclodextrins such as hydroxypropyl-beta-cyclodextrin, beta cyclodextrin, gamma cyclodextrin, and the like, the polysacharides such as starches, gums, and the like polyvinylpyrrolidone, polyvinyl alcohol, the methyl celluloses, sugars, and the like.

A particularly preferred present solid dosage form comprises at least one PGE compound, preferably $PGE_1$, and an alkyl (N-substituted amino) ester, both substantially uniformly distributed in the carrier sheet or admixed with one another in an actives compartment of a packaged paired-compartment dosage form. $PGE_1$ and $PGE_2$ are particularly preferred vasoactive agents for the present purposes.

$PGE_1$ and $PGE_2$ are well known to those skilled in the art. Reference may be had to various literature references for its pharmacological activities, side effects and normal dosage ranges. See for example, *Physician's Desk Reference*, $51^{st}$ Ed. (1997), *The Merck Index*, $12^{th}$ Ed., Merck & Co., N.J. (1996), and *Martindale The Extra Pharmacopoeia*, $28^{th}$ Ed., London, The Pharmaceutical Press (1982). Prostaglandin $E_1$ as well as other PGE compounds referenced herein are intended to compass also the pharmaceutically acceptable derivatives thereof, including physiologically compatible salts and ester derivatives.

The quantity of PGE compound, such as $PGE_1$, present in the solid dosage form is a therapeutically effective amount and necessarily varies according to the desired dose for a particular treatment regimen. The present solid dosage forms can contain about 0.05 to about 25 weight percent of PGE compound, based on the total weight of the composition, preferably about 0.1 to about 15 weight percent of the PGE compound.

A desirable component of the solid dosage form is the skin penetration enhancer. The penetration enhancer can be an alkyl-2-(N-substituted amino)-alkanoate, an (N-substituted amino)-alkanol alkanoate, or a mixture of these. For convenient reference, alkyl-2-(N-substituted amino)-alkanoates and (N-substituted amino)-alkanol alkanoates can be grouped together under the term alkyl (N-substituted amino) esters.

Alkyl-2-(N-substituted amino)-alkanoates suitable for use in the present invention can be represented as follows:

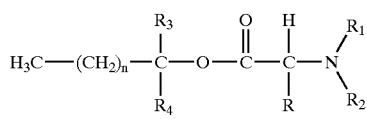

wherein n is an integer having a value in the range of about 4 to about 18; R is a member of the group consisting of hydrogen, $C_1$ to $C_7$ alkyl, benzyl and phenyl; $R_1$ and $R_2$ are members of the group consisting of hydrogen and $C_1$ to $C_7$ alkyl; and $R_3$ and $R_4$ are members of the group consisting of hydrogen, methyl and ethyl.

Preferred are alkyl (N, N-disubstituted amino)-alkanoates such as $C_4$ to $C_{18}$ alkyl(N,N-disubstituted amino)-acetates and $C_4$ to $C_{18}$ alkyl (N,N-disubstituted amino)-propionates and pharmaceutically acceptable salts and derivatives thereof. Exemplary specific alkyl-2-(N,N-disubstituted amino)-alkanoates include dodecyl 2-(N,N-dimethylamino)-propionate;

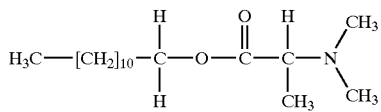

and dodecyl 2-(N,N-dimethylamino)-acetate;

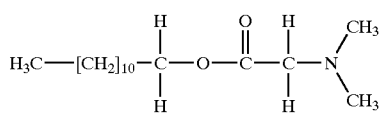

Alkyl-2(N-substituted amino)-alkanoates are known. For example, dodecyl 2-(N,N-dimethylamino)-propionate is available from Steroids, Ltd., Chicago, Ill. In addition, alkyl-2-(N,N-disubstituted amino)-alkanoates can be synthesized from readily available compounds as described in U.S. Pat. No. 4,980,378 to Wong et al., which is incorporated herein by reference to the extent that it is not inconsistent. As described therein, alkyl-2-(N,N-disubstituted amino)-alkanoates are readily prepared via a two-step synthesis. In the first step, long chain alkyl chloroacetates are prepared by reaction of the corresponding long chain alkanols with chloromethyl chloroformate or the like in the presence of an appropriate base such as triethylamine, typically in a suitable solvent such as chloroform. The reaction can be depicted as follows:

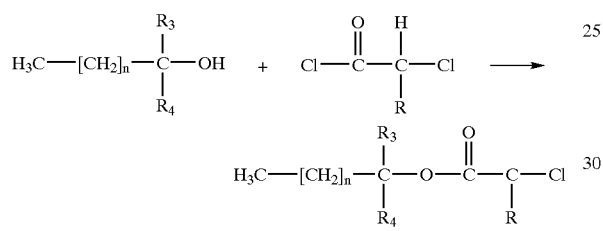

wherein R, $R_3$, $R_4$ and n are defined as above. The reaction temperature may be selected from about 10 degrees Celsius to about 200 degrees Celsius or reflux, with room temperature being preferred. The use of a solvent is optional. If a solvent is used, a wide variety of organic solvents may be selected. Choice of a base is likewise not critical. Preferred bases include tertiary amines such as triethylamine, pyridine and the like. Reaction time generally extends from about one hour to three days.

In the second step, the long chain alkyl chloroacetate is condensed with an appropriate amine according to the scheme:

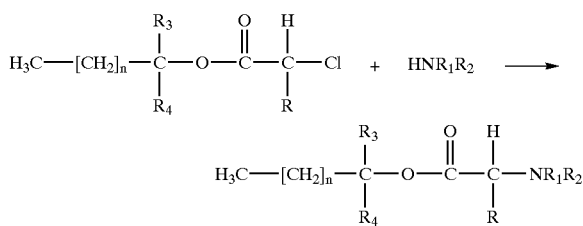

wherein R, $R_1$, $R_2$, $R_3$, and $R_4$ are defined as before. Excess amine reactant is typically used as the base and the reaction is conveniently conducted in a suitable solvent such as ether. This second step is preferably run at room temperature, although temperature may vary. Reaction time usually varies from about one hour to several days. Conventional purification techniques can be applied to ready the resulting ester for use in a pharmaceutical compound.

Suitable (N-substituted amino)-alkanol alkanoates can be represented by the formula:

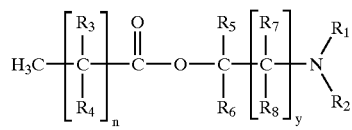

wherein n is an integer having a value in the range of about 5 to about 18; y is an integer having a value in the range of 0 to about 5; and $R_1$, $R_2$, $R_3$, $R_4$ $R_5$, $R_6$ and $R_7$, are members of the group consisting of hydrogen, $C_1$ to $C_8$ alkyl, and $C_1$ to $C_8$ aryl; and $R_8$ is a member of the group consisting of hydrogen, hydroxyl, $C_1$ to $C_8$ alkyl, and $C_1$ to $C_8$ aryl.

Preferred are (N-substituted amino)-alkanol alkanoates such as $C_5$ to $C_{18}$ carboxylic acid esters and pharmaceutically acceptable salts thereof. Exemplary specific (N,N-disubstituted amino)-alkanol alkanoates include 1-(N,N-dimethylamino)-2-propanol dodecanoate;

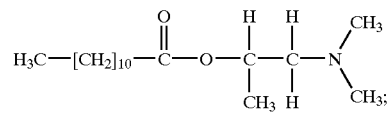

1-(N,N-dimethylamino)-2-propanol myristate;

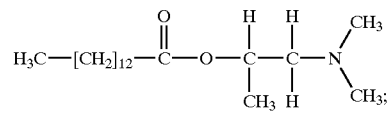

1-(N,N-dimethylamino)-2-propanol oleate;

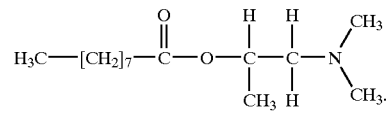

The (N,N-disubstituted amino)-alkanol alkanoates are readily prepared by reacting the corresponding aminoalkinol with lauroyl chloride in the presence of triethylamine. A solvent such as chloroform is optional but preferred. For example, 1-(N,N-dimethylamino)-2-propanol can be reacted with lauroyl chloride in chloroform and in the presence of triethylamine to form 1-(N,N-dimethylamino)-2-propanol dodecanoate.

Among the suitable penetration enhancers for use in the present solid dosage forms dodecyl 2-(N,N-dimethylamino)-propionate and crystalline salts thereof are generally preferred. The preparation of such crystalline salts is described in U.S. Pat. No. 6,118,020 to Buyuktimkin et al.

The penetration enhancer is present in an amount sufficient to enhance the penetration of the PGE compound into tissue. The specific amount varies necessarily according to the desired release rate and specific form of PGE compound used. Generally, this amount is in the range of about 0.01 percent to about 20 percent, based on the total weight of the composition to be administered to a patient.

The desired release rate, including controlled or sustained release of the active compound can also be modulated by selection of the topical delivery vehicle, e.g., a hydrophobic vehicle such as polydimethylsiloxanes and the like. Carboxy-terminated polydimethylsiloxanes can also enhance skin permeation by the active compound.

Natural and modified polysaccharide gums can also be present as part of the carrier sheet or the topical delivery vehicle. Suitable representative gums are the natural and modified galactomannan gums. A galactomannan gum is a carbohydrate polymer containing D-galactose and D-mannose units, or other derivatives of such a polymer. There is a relatively large number of galactomannans, which vary in composition depending on their origin. The galactomannan gum is characterized by a linear structure of β-D-mannopyranosyl units linked (1→4). Single membered α-D-mannopyranosyl units, linked (1→6) with the main chain, are present as side branches. Galactomannan gums include guar gum, which is the pulverized endosperm of the seed of either of two leguminous plants (Cyamposis tetragonalobus and psoraloids) and locust bean gum, which is found in the endosperm of the seeds of the carbotree (ceratonia siliqua). Suitable modified polysaccharide gums include ethers of natural or substituted polysaccharide gums, such as carboxylmethyl ethers, ethylene glycol ethers and propylene glycol ethers.

Other suitable representative gums include agar gum, carrageenan gum, ghatti gum, karaya gum, rhamsan gum and xanthan gum. The composition of the present invention may contain a mixture of various gums, or mixture of gums and acidic polymers.

Gums, and galactomannan gums in particular, are well-known materials. See for instance, *Industrial Gums:Polysaccharides & Their Derivatives*, Whistler R. L. and BeMiller J. N. (eds.), $3^{rd}$ Ed. Academic Press (1992) and Davidson R. L., *Handbook of Water-Soluble Gums and Resin*, McGraw-Hill, Inc., N.Y. (1980). Most gums are commercially available in various forms, commonly a powder, and ready for use in food and topical compositions. For example, locust bean gum in powdered form is available from Tic Gums Inc. (Belcam, Md.).

When present, the polysaccharide gums are present in the range of about 0.1 percent to about 5 percent, based on the total weight of the composition, with the preferred range being in the range of about 0.5 percent to 3 percent. In one preferred embodiment, about 2.5 percent by weight of a polysaccharide gum is present.

An optional alternative to the polysaccharide gum is a polyacrylic acid polymer. A common variety of polyacrylic acid polymer is known generically as "carbomer." Carbomer is polyacrylic acid polymers lightly cross-linked with polyalkenyl polyether. It is commercially available from the B.F. Goodrich Company (Akron, Ohio) under the designation "CARBOPOL™." A particularly preferred variety of carbomer is that designated as "CARBOPOL 940."

Other polyacrylic acid polymers suitable for use are those commercially available under the designation "Pemulen™" (B.F. Goodrich Company) and "POLYCARBOPHIL™" (A. H. Robbins, Richmond, Va.). The Pemulen™ polymers are copolymers of $C_{10}$ to $C_{30}$ alkyl acrylates and one or more monomers of acrylic acid, methacrylic acid or one of their simple esters crosslinked with an allyl ether of sucrose or an allyl ether of pentaerythritol. The POLYCARBOPHIL™ product is polyacrylic acid cross-linked with divinyl glycol.

The concentration of lipophilic compound required necessarily varies according to other factors such as the desired semi-solid consistency and the desired skin penetration promoting effects. Suitably the concentration of lipophilic compound is the range of about 0.5 percent to about 40 percent by weight based on the total weight of the composition. The preferred topical composition contains lipophilic compound in the range of about 7 percent to about 40 percent by weight based on the total weight of the composition.

Where a mixture of aliphatic alcohol and alphatic ester are employed, the suitable amount of alcohol is in the range of about 0.5 percent to about 75 percent. In one preferred embodiment, the amount of alcohol is in the range of about 5 percent to about 15 percent, while that of aliphatic ester is in the range of about 2 percent to about 15 percent (again based on the total weight of the composition). In another preferred embodiment, the amount of alcohol is in the range of about 0.5 percent to about 10 percent, while that of aliphatic ester is in the range from zero percent to about 10 percent (again based on the total weight of the composition).

An optional, but preferred, component is an emulsifier. A suitable emulsifier generally will exhibit a hydrophilic-lipophilic balance number greater than 10. Sucrose esters, and specifically sucrose stearate, can serve as emulsifiers for the composition. Sucrose stearate is a well-known emulsifier available from various commercial sources. When an emulsifier is used, sucrose stearate, present in an amount up to about 2 percent, based on the total weight of the composition, is preferred. The preferred amount of sucrose stearate emulsifier can also be expressed as a weight ratio of emulsifier to polysacharide gum.

Other suitable emulsifiers are the polyoxyethylene sorbitan esters, long chain alcohols, preferably cetostearyl alcohol, and fatty acid glycerides. Suitable polyoxyethylene sorbitan esters include the monolaurate (Tween 20, Span 20) the monopalmitate (Tween 40), the monostearate (Tween 60), and the monooleate (Tween 80) and mixtures thereof. Preferred fatty acid glycerides include glyceryl monooleate, triolean, trimyristin and tristearin.

Another optional ingredient is an antifoam agent, a chemical that reduces the tendency of the finished preparation to generate foam on shaking or agitation. Silicones are the preferred antifoam agents; however, a wide variety of alcohols and lipids exhibit similar properties. With the exception of alcohols, the selected antifoam agent must be effective in relatively small concentrations, and are employed in trace amounts. Illustrative antifoam agents are dimethicone, cetyl dimethicone, dimethicone silylate, dimethiconol, a mixture of dimethicone and hydrated silica, isopropyl alcohol, hexyl alcohol, trimethylsiloxysilicate, triphenyl trimethicone and the like. Particularly preferred antifoam agent is a mixture of dimethicone with an average chain length of 200 to 300 dimethylsiloxane units and hydrated silica, commercially available under the designation SIMETHICONE USP from Dow Corning Corporation, Michigan.

The composition can include a buffer system, if desired. Buffer systems are chosen to maintain or buffer the pH of compositions within a desired range. The term "buffer system" or "buffer" as used herein refers to a solute agent or agents which, when in a water solution, stabilize such solution against a major change in pH (or hydrogen ion concentration or activity) when acids or bases are added thereto. Solute agent or agents which are thus responsible for a resistance or change in pH from a starting buffered pH value in the range indicated above are well known. While there are countless suitable buffers, potassium phosphate monohydrate has proven effective for compositions of the present invention and is preferred.

The final pH value of the pharmaceutical composition may vary within the physiological compatible range. Necessarily, the final pH value is one not irritating to human skin and preferably such that transdermal transport of the PGE compound is facilitated. Without violating this constraint, the pH may be selected to improve PGE compound stability and to adjust consistency when required. In one embodiment, the preferred pH value is about 3.0 to about 7.4, more preferably about 3.0 to about 6.5, most preferably from about 3.5 to about 6.0.

For preferred topical delivery vehicles the remaining component of the composition is water, which is necessarily purified, e.g., deionized water. Such delivery vehicle compositions contain water in the range of more than about 50 to about 95 percent, based on the total weight of the composition. The specific amount of water present is not critical, however, being adjustable to obtain the desired viscosity (usually about 50 cps to about 10,000 cps) and/or concentration of the other components. The topical delivery vehicle preferably has a viscosity of at least about 30 centipoises.

Other known transdermal skin penetration enhancers can also be used to facilitate delivery of the compound of prostaglandin E group. Illustrative are sulfoxides such as dimethylsulfoxide (DMSO) and the like; cyclic amides such as 1-dodecylazacycloheptane-2-one (Azone®, a registered trademark of Nelson Research, Inc.) and the like; amides such as N,N-dimethyl acetamide (DMA) N,N-diethyl toluamide, N,N-dimethyl formamide, N,N-dimethyl octamide, N,N-dimethyl decamide, and the like; pyrrolidone derivatives such as N-methyl-2-pyrrolidone, 2-pyrrolidone, 2-pyrrolidone-5-carboxylic acid, N-(2-hydroxyethyl)-2-pyrrolidone or fatty acid esters thereof, 1-lauryl-4-methoxycarbonyl-2-pyrrolidone, N-tallowalkylpyrrolidones, and the like; polyols such as propylene glycol, ethylene glycol, polyethylene glycol, dipropylene glycol, glycerol, hexanetriol, and the like; linear and branched fatty acids such as oleic, linoleic, lauric, valeric, heptanoic, caproic, myristic, isovaleric, neopentanoic, trimethyl hexanoic, isostearic, and the like; alcohols such as ethanol, propanol, butanol, octanol, oleyl, stearyl, linoleyl, and the like; anionic surfactants such as sodium laurate, sodium lauryl sulfate, and the like; cationic surfactants such as benzalkonium chloride, dodecyltrimethylammonium chloride, cetyltrimethylammonium bromide, and the like; non-ionic surfactants such as the propoxylated polyoxyethylene ethers, e.g., Poloxamer 231, Poloxamer 182, Poloxamer 184, and the like, the ethoxylated fatty acids, e.g., Tween 20, Myrj 45, and the like, the sorbitan derivatives, e.g., Tween 40, Tween 60, Tween 80, Span 60, and the like, the ethoxylated alcohols, e.g., polyoxyethylene (4) lauryl ether (Brij 30), polyoxyethylene (2) oleyl ether (Brij 93), and the like, lecithin and lecithin derivatives, and the like; the terpenes such as D-limonene, α-pinene, β-carene, α-terpineol, carvol, carvone, menthone, limonene oxide, α-pinene oxide, eucalyptus oil, and the like.

Also suitable as skin penetration enhancers are organic acids and esters such as salicyclic acid, methyl salicylate, citric acid, succinic acid, and the like.

PGE compound stabilizers such as organic acids and alcohols, cyclodextrins, coloring agents, rheological agents, and preservatives can be added to the extent that they do not limit penetration of the PGE compound.

The ingredients listed above may be combined in any order and manner that produces a stable composition for ultimately receiving the PGE compound, such as $PGE_1$ and the like, preferably substantially evenly dispersed throughout. One available approach to preparing such compositions involves evenly dispersing the polysaccharide gum (or polyacrylic acid) in a premixed water/buffer solution and then thoroughly homogenizing (i.e., mixing) the resulting mixture. When present, the emulsifier is added to the water/buffer solution before dispersing the polysaccharide gum. Any suitable method of adjusting pH value to the desired level may be used, for example, by adding concentrated phosphoric acid or sodium hydroxide.

The PGE compound, with or without a penetration enhancer, is then combined therewith prior to use with mixing.

The resulting composition is ready for topical, intrameatal, or vaginal administration.

These compositions can be used for prolonged treatment of peripheral vascular disease, male impotency and other disorders treated or treatable by PGE compounds while avoiding low bioavailability and rapid chemical decomposition associated with other delivery methods.

In one embodiment, a preparation ready for administration comprises about 0.01 percent to about 5 percent modified polysaccharide gum; about 0.001 percent to about 1 percent of a PGE compound, preferably $PGE_1$, or a pharmaceutically acceptable salt thereof, a lower alkyl ester thereof and mixtures thereof; about 0.5 percent to about 10 percent dodecyl 2-(N,N-dimethylamino)-propionate or a salt thereof; about 0.5 percent to about 10 percent of a lower alcohol selected from the group consisting of ethanol, propanol, isopropanol and mixtures thereof; about 0.5 percent to about 10 percent on an ester selected from the group consisting of ethyl laurate, isopropyl myristate, isopropyl laurate and mixture thereof; based on the weight of the preparation, together with an acid buffer. Preferably the preparation also comprises up to about 2 percent by weight sucrose stearate.

Variations in the treating compositions which do not adversely affect the effectiveness of the PGE compound will be evident to one skilled in the art, and are within the scope of this invention. For example, additional ingredients such as coloring agents, anti-microbial preservatives, emulsifiers, lubricants, perfumes, PGE compound stabilizers, and the like, may be included as long as the resulting preparation retains desirable properties, as described above. When present, preservatives are usually added in amounts of about 0.05 to about 0.30%. Suitable preservatives include methylparabens (methyl PABA), propylparabens (propyl PABA) and butylhydroxy toluene (BHT). Suitable perfumes and fragrances are known in the art; a suitable fragrance is up to about 5 percent and fragrances are known in the art; a suitable fragrance is up to about 5 percent myrtenol, preferably about 2 percent myrtenol, based on the total weight of the composition. The compositions of the present invention can also include a small amount, about 0.01 to about 4 percent by weight, of a topical anesthetic, if desired. Typical topical anesthetics include lidocaine, benzocaine, dyclonine, dibucaine, pharmaceutically acceptable salts and mixtures thereof. In one preferred embodiment, the topical anesthetic is about 0.5 percent dyclonine, based on the weight of the composition.

Illustrative two-compartment dosage forms are set forth below:

| | Amount, parts by weight | |
|---|---|---|
| | Preferred | More Preferred |
| Actives Compartment | | |
| $PGE_1$ | 0.025–10 | 0.05–0.5 |
| Dodecyl 2-(N,N-dimethylamino)-propionate.HCl | 0.025–10 | 0.05–2.5 |
| Lactose | 1–50 | 2.5–10 |
| Inerts Compartment | | |
| Hydroxypropyl methyl cellulose | 0.05–2.5 | 1–6 |
| Silicone antifoam agent | 0.001–5 | 0.1–2 |
| Hydroxypropyl-β-cyclodextrin | 0.5–25 | 1–10 |

-continued

| | Amount, parts by weight | |
|---|---|---|
| | Preferred | More Preferred |
| Water (deionized or U.S.P.) | 5–75 | 20–60 |
| Ethanol | 5–75 | 20–60 |

If desired, preservatives such as methyl paraben, propyl paraben, benzalkonium chloride, benzethonium chloride, and the like, can be included as well.

Yet another two-compartment dosage form is set forth below:

| | Amount, parts by weight |
|---|---|
| Actives Compartment | |
| $PGE_1$ | 0.2 |
| Dodecyl 2-(N,N-dimethylamino)-propionate.HCl | 2.5 |
| Ethanol, anhydrous, USP | 5 |
| Inerts Compartment | |
| Guar gum | 2.5 |
| Ethyl laurate | 3 |
| Water, USP, buffered to pH 5.5 with 0.1M $KH_2 PO_y$ NF q.s. | 100 |
| Sodium hydroxide, q.s. pH 5.5 | |

Illustrative two-part compositions for casting a $PGE_1$-containing film are set forth below.

| | Amount, parts by weight | |
|---|---|---|
| | Preferred | More Preferred |
| Part A | | |
| $PGE_1$ | 0.025–10 | 0.05–0.5 |
| Dodecyl 2-(N,N-dimethylamino)-propionate.HCl | 0.025–10 | 0.05–2.5 |
| Hydroxypropyl-β-cyclodextrin | 0.05–25 | 1–10 |
| Part B | | |
| Hydroxypropyl methylcellulose | 0.05–25 | 1–6 |
| Polyethylene glycol 8000 powder | 0.05–25 | 0.5–5 |
| Silicone antifoam agent | 0.001–5 | 0.1–2 |
| Hydroxypropyl-β-cyclodextrin | 0.5–25 | 1–10 |
| Water (deionized or U.S.P.) | 5–90 | 20–60 |
| Ethanol | 5–75 | 20–60 |

Parts A and B are combined with agitation, the resulting mixture is cast as a layer on a surface, and the ethanol is permitted to evaporate to produce a sheet-form material, i.e., either a sheet or a film depending upon the thickness of the cast layer.

The present invention is further illustrated by the following examples.

EXAMPLE 1
Two Compartment Packaged Dosage Form

A viscous topical delivery vehicle was prepared by combining hydroxypropyl methyl cellulose (2 grams; Methocel® E4M; Dow Chemical Co.), polyethylene glycol 8000 powder (0.5 grams), deionized water (97.5 grams), and a trace amount of an antifoam agent (Simethicone®; Dow Corning Corp., Midland, Mich.).

First an aliquot of deionized water (about 25 grams) was heated to about 80° C., and then the hydroxypropyl methyl cellulose (2 grams) was added thereto with stirring until dissolved. A trace amount of the anti-foam agent was added to the resulting hot solution.

Polyethylene glycol powder (0.5 grams; PEG 8000, was added to cold deionized water (50 grams) with stirring until dissolved to produce a cold polyethylene glycol solution.

The obtained cold and hot solutions were combined with stirring, more deionized water was added to the combined solution (q.s. 100 grams), and the produced solution was placed in an ice bath and chilled to below about 30° C. with continuous agitation. The pH value of the produced solution was measured as 6.25.

This solution is suitable as constituent for the inerts compartment of the two-compartment dosage form. Ethyl alcohol can be added to produce a solution suitable for casting a sheet-form unit dose such as a film or sheet.

The contents for the actives compartment was prepared by admixing dry prostaglandin $E_1$ (0.018 grams) and dodecyl 2-(N,N-dimethylamino)-propionate (0.12 grams).

The actives content prepared as described hereinabove was then combined with three grams of the inerts composition described above to which anhydrous ethyl alcohol (3 grams) was added.

A clear, viscous gel was obtained, suitable for topical or intrameatal administration. The pH value of the obtained gel was measured as 4.5.

EXAMPLE 2
Film with $PGE_1$ and Skin Permeation Enhancer

A portion of the clear gel produced as described in Example 1 was spread on a glass panel with a 6-mil film spreader and dried for several hours until a film was produced. Upon the addition of a small amount of water (100 milligrams) a one-inch square of film reconstituted into a clear gel within about 15 seconds.

EXAMPLE 3
Film with $PGE_1$ $PGE_1$ powder (0.024 grams) was combined with an aqueous solution having the following constituents:

| | | |
|---|---|---|
| Hydroxypropyl methyl cellulose | 0.06 | grams |
| PEG 8000 powder | 0.015 | grams |
| Deionized water | 2.925 | grams |
| Ethyl alcohol, anhydrous | 3 | grams | and prepared in the same manner as described in Example 1, above. The resulting combination of $PGE_1$ and the aqueous solution was shaken vigorously for 15 to 30 seconds until the $PGE_1$ went into solution.

The resulting solution was poured onto a glass panel and dried at ambient temperature for about 3.5 hours. A film containing $PGE_1$ substantially uniformly dispersed therein was obtained.

EXAMPLE 4
Film with $PGE_1$ and Dodecyl 2-(N,N-Dimethylamino)-propionate

The procedure of Example 3, above, was used to dissolve $PGE_1$ (0.024 grams) and dodecyl 2-(N,N-dimethylamino)-propionate (0.03 grams) in an aqueous solution having the following constituents:

| | |
|---|---|
| Hydroxypropyl methyl cellulose | 0.06 grams |
| PEG 8000 powder | 0.015 grams |
| Deionized water | 2.9 grams |
| Ethyl alcohol, anhydrous | 3 grams |

The obtained solution was poured onto a glass panel, spread with a 6-mil. film spreader, and dried for about 3.5 hours. A dry film containing substantially uniformly dispersed $PGE_1$ and dodecyl 2-(N,N-dimethylamino)-propionate was obtained. The film was readily water miscible.

We claim:

1. A packaged prostaglandin E dosage form which comprises a sealed actives compartment containing about 0.025 to 10 parts by weight of prostaglandin $E_1$, about 0.025 to 10 parts by weight dodecyl 2-(N,N-dimethylamino)-propionate or a salt thereof, and about 1 to 50 parts by weight lactose; and a sealed inerts compartment containing about 0.05 to 2.5 parts by weight hydroxypropyl methylcellulose, about 0.001 to 5 parts by weight silicone antifoam agent, about 0.5 to 25 parts by weight hydroxypropyl-β-cyclodextrin, about 5 to 75 parts by weight ethanol, and about 5 to 75 parts by weight water.

2. A packaged prostaglandin E dosage form which comprises a sealed actives compartment containing about 0.2 parts by weight of prostaglandin $E_1$, about 2.5 parts by weight dodecyl 2-(N,N-dimethylamino)-propionate or a salt thereof, and about 5 parts by weight anhydrous ethanol; and a sealed inerts compartment containing about 2.5 parts by weight guar gum, 3 parts by weight ethyl laurate, and 100 parts by weight water buffered to a pH of about 5.5.

* * * * *